US00PP26635P2

(12) United States Plant Patent
Geibel

(10) Patent No.: US PP26,635 P2
(45) Date of Patent: Apr. 19, 2016

(54) ***PELARGONIUM* PLANT NAMED 'PACSALLY'**

(50) Latin Name: *Pelargonium peltatum*
Varietal Denomination: Pacsally

(71) Applicant: Martin Geibel, Dresden (DE)

(72) Inventor: Martin Geibel, Dresden (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 152 days.

(21) Appl. No.: 13/999,902

(22) Filed: Apr. 1, 2014

(51) Int. Cl.
*A01H 5/00* (2006.01)

(52) U.S. Cl.
USPC ..... Plt./332

(58) Field of Classification Search
USPC ..... Plt./332
See application file for complete search history.

*Primary Examiner* — Keith Robinson
(74) *Attorney, Agent, or Firm* — C. A. Whealy

(57) ABSTRACT

A new and distinct Ivy Geranium plant named 'Pacsally', characterized by its uniformly mounded and cascading to trailing plant habit; moderately vigorous growth habit; freely basal branching habit; freely flowering habit; and large dark red-colored semi-double flowers held above the foliar plane.

1 Drawing Sheet

Botanical designation: *Pelargonium peltatum.*
Cultivar denomination: 'PACSALLY'.

BACKGROUND OF THE INVENTION

The present invention relates to a new and distinct cultivar of Ivy Geranium plant, botanically known as *Pelargonium peltatum*, and hereinafter referred to by the name 'Pacsally'.

The new Ivy Geranium plant is a product of a planned breeding program conducted by the Inventor in Dresden, Germany. The objective of the breeding program is to develop new vigorous Ivy Geranium plants with uniform plant habit and numerous semi-double flowers.

The new Ivy Geranium plant originated from a cross-pollination made by the Inventor in Dresden, Germany during the summer of 2006 of two unnamed proprietary selections of *Pelargonium peltatum*, not patented. The new Ivy Geranium plant was discovered and selected by the Inventor as a flowering plant from within the progeny of the stated cross-pollination in a controlled greenhouse environment in Dresden, Germany in June, 2007.

Asexual reproduction of the new Ivy Geranium plant by vegetative terminal cuttings in a controlled greenhouse environment in Dresden, Germany since December, 2007 has shown that the unique features of this new Ivy Geranium plant are stable and reproduced true to type in successive generations.

SUMMARY OF THE INVENTION

Plants of the new Ivy Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pacsally'. These characteristics in combination distinguish 'Pacsally' as a new and distinct Ivy Geranium plant:

1. Uniformly mounded and cascading to trailing plant habit.
2. Moderately vigorous growth habit.
3. Freely basal branching habit.
4. Freely flowering habit.
5. Large dark red semi-double flowers held above the foliar plane.

Plants of the new Ivy Geranium differ primarily from plants of the parent selections in flower coloration. In addition, plants of the new Ivy Geranium are more uniform than plants of the parent selections.

Plants of the new Ivy Geranium can be compared to plants of the *Pelargonium peltatum* 'Pactomgi', disclosed in U.S. Plant Pat. No. 13,780. In side-by-side comparisons conducted in Dresden, Germany, plants of the new Ivy Geranium differed from plants of 'Pactomgi' in the following characteristics:

1. Plants of the new Ivy Geranium were more trailing than and not as upright as plants of 'Pactomgi'.
2. Plants of the new Ivy Geranium were more vigorous than plants of 'Pactomgi'.
3. Plants of the new Ivy Geranium had smaller leaves than plants of 'Pactomgi'.
4. Plants of the new Ivy Geranium had larger flowers than plants of 'Pactomgi'.
5. Flowers of plants of the new Ivy Geranium had fewer petals than flowers of plants of 'Pactomgi'.

BRIEF DESCRIPTION OF THE PHOTOGRAPH

The accompanying colored photograph illustrates the overall appearance of the new Ivy Geranium plant showing the colors as true as it is reasonably possible to obtain in colored reproductions of this type. Colors in the photograph may differ slightly from the color values cited in the detailed botanical description which accurately describe the colors of the new Ivy Geranium plant.

The photograph comprises a side perspective view of a typical flowering plant of 'Pacsally' grown in a container.

DETAILED BOTANICAL DESCRIPTION

The aforementioned photograph and following observations, measurements and values describe plants grown in 19-cm containers during the summer and autumn in a glass-covered greenhouse in Dresden, Germany and under cultural practices typical of commercial Ivy Geranium production. During the production of the plants, day temperatures ranged from 18° C. to 20° C., night temperatures averaged 18° C. and light levels ranged from 15 kilolux to 100 kilolux. Plants were pinched two times and were seven months old when the photograph was taken and nine months old when the detailed description was taken. In the detailed description, color references are made to The Royal Horticultural Society Colour Chart, 1995 Edition, except where general terms of ordinary dictionary significance are used.

Botanical classification: *Pelargonium peltatum* 'Pacsally'.

Parentage:

*Female, or seed, parent*.—Unnamed proprietary selection of *Pelargonium peltatum*, not patented.

*Male or pollen parent*.—Unnamed proprietary selection of *Pelargonium peltatum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer and winter*.—About four weeks at temperatures about 20° C.

*Root description*.—Fine, fibrous.

*Rooting habit*.—Freely branching; dense.

Plant description:

*Plant and growth habit*.—Uniformly mounded and cascading to trailing plant habit; broad inverted triangle; densely foliated; moderately vigorous growth habit; freely basal branching habit with numerous lateral branches developing per plant.

*Plant height, to top of umbels*.—About 35 cm.

*Plant height, to top of foliar plane*.—About 25 cm.

*Plant width*.—About 50 cm.

*Lateral branches*.—Length: About 50 cm. Diameter: About 4 mm. Internode length: About 3 cm. Texture: Slightly pubescent. Color: Close to 144A.

Leaf description:

*Arrangement*.—Opposite; simple.

*Length*.—About 3.5 cm.

*Width*.—About 7 cm.

*Shape*.—Palmately lobed.

*Apex*.—Rounded.

*Base*.—Cordate, closed.

*Margin*.—Entire, lobed.

*Venation pattern*.—Palmate.

*Texture, upper and lower surfaces*.—Slightly pubescent; leathery.

*Color*.—Developing and fully expanded leaves, upper surface: Close to 137A; venation, close to 144A. Developing and fully expanded leaves, lower surface: Close to 137C; venation, close to 144A. Zonation pattern: Intensity: Distinct. Location: About 2.5 cm from margin. Width: About 1 cm. Color: Close to 200C.

*Petioles*.—Length: About 4 cm. Diameter: About 2 mm. Texture, upper and lower surfaces: Slightly rough. Color, upper and lower surfaces: Close to 144A.

Flower description:

*Flower arrangement and flowering habit*.—Semi-double flowers arranged in roughly hemispherical umbels arising from apical leaf axils; umbels displayed above the foliar plane on strong flexible peduncles; flowers face upright to outwardly; freely flowering habit; about six flowers per umbel.

*Fragrance*.—None detected.

*Flowering season*.—Early flowering habit, plants begin flowering about four months after planting; in the garden in Germany, flowering begins in May and continues until frost.

*Flower longevity*.—Flowers last about six to ten days on the plant; umbels last about three to four weeks on the plant; flowers persistent.

*Umbel height*.—About 6 cm.

*Umbel diameter*.—About 10 cm.

*Flower diameter*.—About 6 cm.

*Flower depth* (*height*).—About 2 cm.

*Flower buds*.—Length: About 1 cm. Diameter: About 5 mm. Shape: Spindle-shaped. Color: Close to 144A.

*Petals*.—Quantity per flower: About nine in about two whorls; petals somewhat imbricate. Length: About 3.2 cm. Width: About 2 cm. Shape: Obovate. Apex: Rounded. Base: Cuneate. Margin: Entire. Texture, upper and lower surfaces: Smooth, glabrous; velvety; undulate. Color: When opening and fully opened, upper surface: Close to 46A; towards the base, close to 155D; venation, close to 187A; with development, color does not change. When opening and fully opened, lower surface: Close to 47A; towards the base, close to 155D; venation, close to 187A.

*Petaloids*.—Quantity per flower: About three to six. Length: About 1 cm to 2 cm. Width: About 4 mm to 8 mm. Shape: Irregular. Apex: Rounded. Base: Cuneate. Margin: Entire. Texture, upper and lower surfaces: Smooth, glabrous; velvety; crinkled. Color: When opening and fully opened, upper surface: Close to 46A; towards the base, close to 155D; venation, close to 187A; with development, color becoming closer to 46B. When opening and fully opened, lower surface: Close to 47A; towards the base, close to 155D; venation, close to 53A.

*Sepals*.—Quantity per flower: About five or six arranged in a single whorl. Length: About 1.4 cm. Width: About 3 mm. Shape: Lanceolate. Apex: Acute. Margin: Entire. Texture, upper and lower surfaces: Slightly pubescent. Color, upper and lower surfaces: Close to 144A.

*Peduncles* (*umbel stems*).—Length: About 12 cm. Diameter: About 3 mm. Strength: Strong, flexible. Angle: Upright to outwardly slanted. Texture: Slightly pubescent. Color: Close to 144A.

*Pedicels* (*individual flower stems*).—Length: About 3.6 cm. Diameter: About 2 mm. Strength: Strong; flexible. Texture: Pubescent. Color: Close to 144A.

*Reproductive organs*.—Androecium: Stamen quantity per flower: About ten. Anther length: About 2 mm. Anther shape: Tubular. Anther color: Close to 72A.

Pollen amount: Moderate. Pollen color: Close to 171A. Gynoecium: Pistil quantity per flower: One. Pistil length: About 1.2 cm. Stigma shape: Five-parted. Stigma color: Close to 61A. Style length: About 3 mm. Style color: Close to 155D. Ovary color: Close to 147C. Seeds and fruits: Seed and fruit development have not been observed on plants of the new Ivy Geranium.

Disease & pest resistance: Plants of the new Ivy Geranium have not been observed to be resistant to pathogens and pests common to Ivy Geranium plants.

Temperature tolerance: Plants of the new Ivy Geranium have been observed to tolerate temperatures ranging from about 1° C. to about 35° C. to 40° C.

It is claimed:

1. A new and distinct Ivy Geranium plant named 'Pacsally' as illustrated and described.

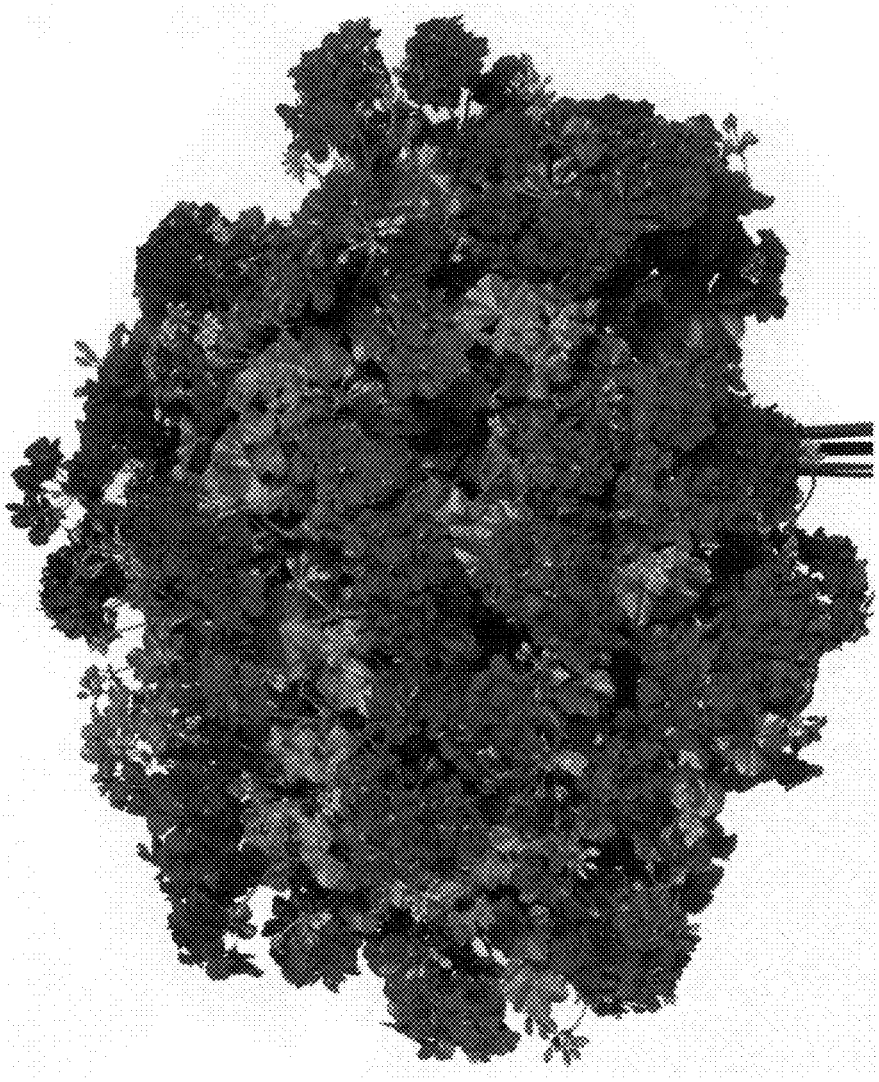

* * * * *